United States Patent
Bekemeier et al.

(10) Patent No.: US 11,207,263 B2
(45) Date of Patent: Dec. 28, 2021

(54) COSMETIC COMPOSITIONS

(71) Applicant: Dow Silicones Corporation, Midland, MI (US)

(72) Inventors: Thomas Bekemeier, Birch Run, MI (US); Patrick Fryfogle, Sanford, MI (US); Gary Wieber, Midland, MI (US); Kimmai Nguyen, Midland, MI (US); Zhi Li, Audubon, PA (US); Julie Cook, Turner, MI (US); Jason Vogel, Freeland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 16/624,152

(22) PCT Filed: Jun. 15, 2018

(86) PCT No.: PCT/US2018/037683
§ 371 (c)(1),
(2) Date: Dec. 18, 2019

(87) PCT Pub. No.: WO2019/045830
PCT Pub. Date: Mar. 7, 2019

(65) Prior Publication Data
US 2020/0237639 A1 Jul. 30, 2020

Related U.S. Application Data (60) Provisional application No. 62/552,481, filed on Aug. 31, 2017.

(51) Int. Cl.
| | |
|---|---|
| *A61K 8/891* | (2006.01) |
| *A61K 8/19* | (2006.01) |
| *A61K 8/86* | (2006.01) |
| *A61Q 1/02* | (2006.01) |
| *A61Q 1/10* | (2006.01) |
| *A61Q 3/00* | (2006.01) |
| *A61Q 19/00* | (2006.01) |

(52) U.S. Cl.
CPC .............. *A61K 8/891* (2013.01); *A61K 8/19* (2013.01); *A61K 8/86* (2013.01); *A61Q 1/025* (2013.01); *A61Q 1/10* (2013.01); *A61Q 3/00* (2013.01); *A61Q 19/00* (2013.01)

(58) Field of Classification Search
CPC ........ C08G 65/04; C08G 77/12; C08G 77/20; C08G 77/70; A61K 8/89
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,296,291 A | 1/1967 | Chalk | |
| 3,419,593 A | 12/1968 | Willing | |
| 3,516,946 A | 6/1970 | Modic | |
| 3,814,730 A | 6/1974 | Karstedt | |
| 3,928,629 A | 12/1975 | Chandra et al. | |
| 3,989,668 A | 11/1976 | Lee et al. | |
| 5,036,117 A | 7/1991 | Chung et al. | |
| 5,175,325 A | 12/1992 | Brown et al. | |
| 5,369,205 A * | 11/1994 | Eckberg ................. | C08G 77/46 522/148 |
| 6,605,734 B2 | 8/2003 | Roy et al. | |
| 2010/0000307 A1 | 1/2010 | Slayne | |

FOREIGN PATENT DOCUMENTS

| | | |
|---|---|---|
| EP | 465744 | 1/1992 |
| WO | 2010001221 | 1/2010 |

\* cited by examiner

*Primary Examiner* — Kuo Liang Peng (57) ABSTRACT

This invention relates to a cosmetic composition comprising: (A) a film forming composition that can produce a tack free surface comprising: (I) a hydrosilylation reaction product of: (a) a silicone resin having the formula: $(R^1R^2{}_2SiO_{1/2})_w(R^1R^2SiO_{2/2})_x(R^2SiO_{3/2})_y(SiO_{4/2})_z$ wherein $R^2$ is a $C_1$ to $C_{10}$ hydrocarbon group free of aliphatic unsaturation, $R^1$ is $R^2$ or an alkenyl group, w is from 0.3 to 0.6, x is from 0.0 to 0.2, y is 0, z is from 0.4 to 0.7, w+x+y+z=1.0, and w+z is from 0.85 to 1.0, with the proviso that the silicone resin (a) has at least two silicon-bonded alkenyl groups per number average molecule; (b) a polyether compound having the formula: $R^3O(C_2H_4O)_c(C_3H_6O)_dR^3$ wherein $R^3$ is a monovalent unsaturated aliphatic hydrocarbon group containing 2 to 12 carbon atoms, c is from 0 to 50, d is from 0 to 50, and the value of c+d is greater than zero; (c) an SiH functional organopolysiloxane having the general formula: $H_cR_{3-c}SiO(R_2SiO)_a(RHSiO)_bSiR_{3-c}H_c$ wherein c is 0 or 1, R can be identical or different and is a monovalent, optionally substituted hydrocarbon group with 1 to 18 carbon atoms per molecule, a and b are integers, with the proviso that the sum of a+b is 0 to 300, and wherein the organopolysiloxane contains SiH in amounts from 0.01 to 0.4 wt %; (d) a hydrosilylation catalyst; and (e) carrier solvent; and (II) a silicone resin having the formula: $(R^4{}_3SiO_{1/2})_u(SiO_{4/2})_v$ wherein $R^4$ is a $C_1$ to $C_{10}$ to do hydrocarbon group free of aliphatic unsaturation, u is from 0.3 to 0.6, v is from 0.4 to 0.7, and the value of u+v is 1.0; and (B) at least one cosmetic ingredient.

17 Claims, 3 Drawing Sheets

COSMETIC COMPOSITIONS

CROSS-REFERENCE TO RELATED APPLICATIONS

This application claims the benefit of U.S. Provisional Patent Application Ser. No. 62/552,481 filed on 31 Aug. 2017 under 35 U.S.C. § 119 (e). U.S. Provisional Patent Application Ser. No. 62/552,481 is hereby incorporated by reference.

BACKGROUND OF THE INVENTION

This invention relates to a cosmetic composition that can form a tack free film on the surface of a substrate. In cosmetics, and particularly in beauty care, the ability of a cosmetic composition to be tack free is very advantageous. In general, cosmetic compositions containing silicone film forming compositions are known in the art, with the most widely used silicone film former being an MQ resin. MQ resins form a continuous film but are inflexible. Silicone-based alternatives to MQ resins are often more flexible but impart to the film a tacky feel on the skin. This invention offers flexibility to beauty care compositions without a imparting a tacky feel. Additionally, this invention imparts improved sebum resistance in cosmetic compositions compared to benchmark formulations.

BRIEF SUMMARY OF THE INVENTION

This invention relates to a cosmetic composition comprising: (A) a film forming composition that can produce a tack free surface comprising: (I) a hydrosilylation reaction product of: (a) a silicone resin having the formula: $(R^1R^2{}_2SiO_{1/2})_w(R^1R^2SiO_{2/2})_x(R^2SiO_{3/2})_y(SiO_{4/2})_z$ wherein $R^2$ is a $C_1$ to $C_{10}$ hydrocarbon group free of aliphatic unsaturation, $R^1$ is $R^2$ or an alkenyl group, w is from 0.3 to 0.6, x is from 0.0 to 0.2, y is 0, z is from 0.4 to 0.7, w+x+y+z=1.0, and w+z is from 0.85 to 1.0, with the proviso that the silicone resin (a) has at least two silicon-bonded alkenyl groups per number average molecule; (b) a polyether compound having the formula: $R^3O(C_2H_4O)_c(C_3H_6O)_dR^3$ wherein $R^3$ is a monovalent unsaturated aliphatic hydrocarbon group containing 2 to 12 carbon atoms, c is from 0 to 50, d is from 0 to 50, and the value of c+d is greater than zero; (c) an SiH functional organopolysiloxane having the general formula: $H_cR_{3-c}SiO(R_2SiO)_a(RHSiO)_bSiR_{3-c}H_c$ wherein c is 0 or 1, R can be identical or different and is a monovalent, optionally substituted hydrocarbon group with 1 to 18 carbon atoms per molecule, a and b are integers, with the proviso that the sum of a+b is 0 to 300, and wherein the organopolysiloxane contains SiH in amounts from 0.01 to 0.4 wt % H; (d) a hydrosilylation catalyst; and (e) carrier solvent; and (II) a silicone resin having the formula: $(R^4{}_3SiO_{1/2})_u(SiO_{4/2})_v$ wherein $R^4$ is a $C_1$ to $C_{10}$ hydrocarbon group free of aliphatic unsaturation, u is from 0.3 to 0.6, v is from 0.4 to 0.7, and the value of u+v is 1.0; and (B) at least one cosmetic ingredient.

DETAILED DESCRIPTION OF THE INVENTION

In the hydrosilylation reaction product, component (a), the silicone resin, the alkenyl groups represented by $R^1$, which may be the same or different, typically have from 2 to about 10 carbon atoms, alternatively from 2 to 6 carbon atoms, and are exemplified by, but not limited to vinyl, allyl, butenyl, hexenyl, and octenyl. The silicone resin typically contains less than 9 mol % alkenyl groups attached to silicon relative to the sum of all silicon atoms in the alkenyl-functional MQ resin which totals 100 mol %, preferably, the alkenyl-functional MQ resin contains 1 to 7 mol % alkenyl groups, and more preferably 2 to 5 mol % alkenyl groups. The silicone resin typically has a weight-average molecular weight ($M_w$) of from 1,000 to 50,000 Daltons, alternatively from 2,000 to 30,000, alternatively 3,000 to 25,000 where the molecular weight is determined by gel permeation chromatography employing a light-scattering detector, a refractive index detector, and a viscosity detector and employing polystyrene standards. The silicone resin is typically delivered in a hydrocarbon or silicone solvent, free from solvent the silicone resin is typically a solid. Non-limiting examples of hydrocarbon solvents are aliphatic hydrocarbons, aromatic hydrocarbons, alcohols, esters, ethers, glycols, or ketones. Alternatively, the silicone resin could be delivered in a silicone solvent. Non-limiting examples of silicone solvents could be linear or cyclic polydimethylsiloxanes. The silicone resin typically contains less than 5% (w/w), alternatively less than 2% (w/w), alternatively less than 1.2% (w/w), of silicon-bonded hydroxy groups, as determined by NMR. The silicone resin can be a single silicone resin or a mixture comprising two or more different silicone resins, each as described above. Alternatively component (a) is a silicone resin having the formula: $(R^1R^2{}_2SiO_{1/2})_w(SiO_{4/2})_z$ wherein $R^1$ is vinyl, $R^2$ is methyl, w is from 0.3 to 0.6, z is from 0.4 to 0.7, and the value of w+z is 1.0.

Methods of preparing silicone resins are well known in the art. In some aspects, the resin is made by treating a resin copolymer produced by a silica hydrosol capping process with an alkenyl containing endblocking agent. This preferably includes reacting a silica hydrosol under acidic conditions with a hydrolysable triorganosilane such as trimethylchlorosilane, a siloxane such as hexamethyldisiloxane, and combinations thereof, and then recovering a copolymer having M ($R_3SiO_{1/2}$) units and Q ($SiO_{4/2}$) units including 2 to 5 wt % hydroxyl groups. The copolymer may be further reacted with an endblocking agent including unsaturated organic groups and an endblocking agent free of aliphatic unsaturation in amounts sufficient to provide 3 to 9 mol % of unsaturated organofunctional M or D units in the resin relative to the sum of all M, D ($R_2SiO_{2/2}$) units, and Q units comprising the resin. Suitable endblocking agents include silazanes, siloxanes, silanes, and combinations thereof.

With regard to component (b), the polyether, the value of c is from 0 to 50, alternatively from 0 to 24, or alternatively 0 to 14, and the value of d is form 0 to 50, alternatively from 0 to 20, or alternatively 0 to 7. The polyoxyalkylene useful as this component is a polyoxyalkylene that is terminated at each molecular chain end (i.e. alpha and omega positions) with an unsaturated aliphatic hydrocarbon group containing 2 to 12 carbon atoms. The polyoxyalkylene may result from the polymerization of ethylene oxide or propylene oxide.

The polyoxyalkylene group may comprise oxyethylene units ($C_2H_4O$) or oxypropylene units ($C_3H_6O$). Typically, the polyoxyalkylene group comprises a majority of polyoxyethylene groups. In some embodiments a combination of two or more polyoxyalkylene groups can be advantageous. The unsaturated aliphatic hydrocarbon group can be an alkenyl or alkynyl group. Representative non-limiting examples of the alkenyl groups are: $H_2C=CH-$, $H_2C=CH-CH_2-$, $H_2C=C(CH_3)CH_2-$, $H_2C=CHCH_2CH_2-$, $H_2C=CHCH_2CH_2CH_2$, and $H_2C=CHCH_2CH_2CH_2CH_2-$. Representative, non-limiting examples of alkynyl groups are: $HC\equiv C-$, $HC\equiv CCH_2-$, $HC\equiv CC(CH_3)H-$, $HC\equiv CC(CH_3)_2-$, $HC\equiv CC(CH_3)_2CH_2-$. In one embodiment, the polyoxyalkylene is selected from $H_2C=C(CH_3)CH_2O(C_2H_4O)_cCH_2(CH_3)C=CH_2$ and $H_2C=C(CH_3)CH_2O(C_3H_6O)_dCH_2(CH_3)C=CH_2$ where c and d are defined as above.

Polyoxyalkylenes having an unsaturated aliphatic hydrocarbon group at each molecular terminus are known in the art, and many are commercially available. Polyoxyalkylenes having an unsaturated aliphatic hydrocarbon group at each molecular terminal are commercially available from NOF (Nippon Oil and Fat, Tokyo, Japan) and Clariant Corp. (Muttenz, Switzerland).

With regard to component (c), the Si—H functional organopolysiloxane, c is 0 or 1, R can be identical or different and is a monovalent, optionally substituted hydrocarbon with 1 to 18 carbon atoms per molecule, a and b are integers, with the proviso that the sum of a+b is 0 to 300, alternatively 4 to 200, alternatively 6 to 110, and that component (c) contains Si-bonded hydrogen in amounts from 0.01 to 0.4 wt %, preferably 0.02 to 0.2 wt %, more preferably 0.025 to 0.09 wt %. In a preferred embodiment, b is 0; c is 1; and a is from 6 to 110. R can be an alkyl group or aryl group optionally substituted with hyrdrocarbon groups such as methyl, ethyl, propyl, butyl, hexyl, pentyl, octyl, and decyl, or an aryl group such as phenyl. In one aspect, R is methyl. Component (c) can further comprise two or more SiH functional organopolysiloxanes which can be the same or different as desired. Alternatively (c) is an SiH functional organopolysiloxane having the general formula: $HR_2SiO(R_2SiO)_a(RHSiO)_bSiR_2H$ wherein R is methyl the sum of a+b is 4 to 200 or alternatively 6 to 110.

Component (d) the hydrosilylation catalyst can be any catalyst typically employed for hydrosilylation reactions. Typically the hydrosilylation catalyst is any platinum group metal-containing catalyst. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629. The platinum group-containing catalyst can be platinum group metal, platinum group metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. Pat. No. 6,605,734, such as $(COD)Pt(SiMeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$. The appropriate amount of the catalyst will depend upon the particular catalyst used. The platinum catalyst should be present in an amount sufficient to provide at least 2 parts per million (ppm), alternatively 4 to 200 ppm of platinum based on total weight percent solids (all non-solvent ingredients) in the composition. Typically, the platinum is present in an amount sufficient to provide 4 to 150 weight ppm of platinum on the same basis. The catalyst may be added as a single species or as a mixture of two or more different species.

Generally, the carrier solvent, component (e), comprises at least one miscible fluid that is sufficiently compatible with the reaction mixture. In some aspects; suitable miscible fluids may be selected from silicones and organic compounds and mixtures thereof. Alternatively, the solvent could be a silicone polyether. Examples of suitable silicone carrier solvents include but are not limited to, low molecular weight linear or cyclic volatile silicones; non-volatile alkyl or aryl silicones; and low molecular weight linear or cyclic functional silicones. The silicone miscible fluid may be a single silicone or a mixture of silicones. In some aspects, the solvent is a low molecular weight volatile methyl silicone (VMS) having an average unit formula of $(CH_3)_xSiO_{(4-x)/2}$ in which x has an average value of from 2 to 3. Representative units in such VMS compounds are $(CH_3)_3SiO_{1/2}$ units and $(CH_3)_2SiO_{2/2}$ units, and there additionally may be $CH_3SiO_{3/2}$ units and/or $SiO_{4/2}$ units that result in the formulation of branched, linear or cyclic volatile methyl silicones. Linear VMS have the formula $(CH_3)_3SiO\{(CH_3)_2SiO\}_ySi(CH_3)_3$ where y is 0 to 5. Cyclic VMS have the formula $\{(CH_3)_2SiO\}_z$ where z is 3 to 6. Typically these volatile methyl silicones have boiling points less than about 250° C. and viscosities from about 0.65 to 5.0 centistokes ($mm^2/s$).

In some aspects, suitable silicone carrier solvents include, but are not limited to, linear volatile methyl silicones, such as hexamethyldisiloxane, octamethyltrisiloxane, decamethyltetrasiloxane, dodecamethylpentasiloxane, tetradecamethylhexasiloxane, hexadecamethylheptasiloxane, cyclic volatile methyl silicones, such as hexamethylcyclotrisiloxane, octamethylcyclotetrasiloxane, decamethylcyclopentasiloxane, and dodecamethylcyclohexasiloxane; and branch volatile methyl silicones, such as a heptamethyl-3-{(trimethylsilyl)oxy}trisiloxane, hexamethyl-3,3, bis-{(trimethylsilyl)oxytrisiloxane, and pentamethyl {(trimethylsilyl)oxy}cyclotrisiloxane.

In some aspects, suitable non-volatile alkyl or arylsilicones that can be used as a carrier solvent include, but are not limited to, linear poly alkyl or aryl silicones; such as compounds of the formula $R^4_3SiO(R^4_2SiO)_mSiR^4_3$; and cyclic poly alkyl or aryl silicones, such as compounds of the formula $(R^4_2SiO)_n$ wherein $R^4$ is an alkyl group of 1 to 6 carbon atoms, or an aryl group such as phenyl, m has a value of 0 to 80, preferably from 0 to 20 and n has a value of 0 to 9, preferably 4 to 6. These silicones have viscosities generally in the range of about 1 to 100 centistokes ($mm^2/s$). Other representative low molecular weight non-volatile silicones have the general structure $R^5_3SiO(R^5R^6SiO)_pSiR^5_3$ where p has a value to provide polymers with a viscosity in the range of about 100 to 10,000 centistokes ($mm^2/s$) and $R^5$ and $R^6$ are alkyl radicals of 1 to 30 carbon atoms, or an aryl group such as phenyl. Typically, the value of p is about 60 to 600. Non-volatile polysiloxanes may be exemplified by, but are not limited to, polydimethylsiloxane, polydiethylsiloxane, polymethylethylsiloxane, polymethylphenylsiloxane, and polydiphenylsiloxane.

In some aspects, suitable organic carrier solvents include isododecane, isohexadecane, ethyl acetate, ethyl alcohol, isopropyl alcohol, ester palmitate, propylene glycol, C12-15 alkyl benzoate, caprylic/capric triglyceride, coco-caprylate/caprate, diisopropyl adipate, propyl propionate, isobutyl acetate, diisostearyl fumarate, diethyl carbonate, dicaprylyl carbonate, dicaprylyl ether, propylene carbonate, diisostearyl malate, isocetyl stearate, isopropyl isostearate, isopropyl laurate, isopropyl myristate, isopropyl palmitate, isopropyl stearate, isostearyl benzoate, myristyl ether acetate w/propylene glycol, myristyl lactate, octyldodecyl stearoyl stearate, octylpalmitate, octylstearate, tridecyl neopentanoate, triisocetyl citrate, lauryl alcohol, oleyl alcohol, glyceryl trioctanate, polyglyceryl-3 diisostearate, mineral oil, dipropylene glycol, glycol ether, propylene glycol methylether acetate, propylene glycol methylether, diethylhexyl carbonate, glycerin, castor oil, lanolin oil, sunflower oil, C11-12 isoparaffin, polydecene, organic fats, oils, fatty acids, fatty alcohols, their derivatives and combinations thereof may also be used.

Component (II) in the film forming composition of the invention is a silicone resin having the formula: $(R^4_3SiO_{1/2})_u(SiO_{4/2})_v$, wherein $R^4$ is a $C_1$ to $C_{10}$ hydrocarbon group free of aliphatic unsaturation, u is from 0.3 to 0.6, v is from 0.4 to 0.7, and the value of u+v is 1.0. $R^4$ can be an alkyl group or aryl group free of aliphatic unsaturation such as methyl, ethyl, propyl, butyl, hexyl, pentyl, octyl, and decyl, or an aryl group such as phenyl. In one aspect, $R^4$ is methyl. The silicone resin of Component (II) typically has a weight-average molecular weight ($M_W$) of from 1,000 to 50,0000 Daltons, alternatively from 2,000 to 30,000, alternatively 3,000 to 25,000 where the molecular weight is determined by gel permeation chromatography employing a light-scattering detector, a refractive index detector, and a viscosity detector and employing polystyrene standards. The silicone resin of Component (II) is typically delivered in a hydrocarbon or silicone solvent, free from solvent the silicone resin is typically a solid. Non-limiting examples of hydrocarbon solvents are aliphatic hydrocarbons, aromatic hydrocarbons, alcohols, esters, ethers, glycols, or ketones. Alternatively, the silicone resin could be delivered in a silicone solvent. Non-limiting examples of silicone solvents could be linear or cyclic polydimethylsiloxanes. The silicone resin of (II) typically contains less than 5% (w/w), alternatively less than 4% (w/w), alternatively less than 3.5 wt % (w/w), of silicon-bonded hydroxy groups, as determined by NMR. The silicone resin of (II) can be a single silicone resin or a mixture comprising two or more different silicone resins, each as described above. Methods of preparing silicone resins are well known in the art. In some aspects, the resin is made by treating a resin copolymer produced by a silica hydrosol capping process with an alkyl containing endblocking agent. This preferably includes reacting a silica hydrosol under acidic conditions with a hydrolysable triorganosilane such as trimethylchlorosilane, a siloxane such as hexamethyldisiloxane, and combinations thereof, and then recovering a copolymer having M and Q groups including 2 to 5 wt % hydroxyl groups. The silicone resin of Component (II) can then be solvent exchanged into a carrier solvent or delivered as a flake or powder.

The hydrosilylation reaction product is the reaction product of components (a) through (e) above and is accomplished by mixing the ingredients together using any known methods in the art, including stirring them together, using equipment such as a mechanical stirrer, simple propeller mixers, Brookfield counter-rotating mixers, or homogenizing mixers. The ingredients can be mixed together at room temperature or can be heated, for example at a temperature of 50 to 110° C. In the reaction, one or more alkenyl functional silicone resins (component (a)) and one or more polyethers (component (b)) can be reacted with one or more SiH functional organopolysiloxanes (component (c)) in the presence of a hydrosilylation catalyst (component (d)) and carrier solvent (e) in a single reaction step. In various embodiments the alkenyl functional silicone resin (a) could be reacted with the SiH functional organopolysiloxane (c) with a molar excess of SiH. The remaining SiH groups could then be reacted with the alkenyl polyether. In another embodiment, the alkenyl polyether (b) could be reacted with the SiH functional organopolysiloxane (c) with a molar excess of SiH. The remaining SiH groups could then be reacted with the alkenyl polyether.

The hydrosilylation reaction product includes residual alkenyl or SiH functionality (e.g. as the result of the reaction between the alkenyl functional silicone resin (a), the alkenyl polyether (b), and the SiH functional organopolysiloxane (c). In various embodiments, the alkenyl or SiH functionality may be observed on a parts per million (ppm) or parts per billion (ppb) level, based on a total weight of the hydrosilylation reaction product. In other embodiments, the alkenyl or SiH functionality is understood based on a molar ratio of alkenyl to SiH functionality of the reactants (e.g. the alkenyl polyether, SiH functional organopolysiloxane, and alkenyl functional silicone resin). For example, the ratio of alkenyl to SiH units used to form the hydrosilylation product may be from 10:1 or 1:10. In various embodiments, this ratio can range from 8:1 to 1.5:1, or preferably from 6:1 to 2:1, and most preferably from 4:1 to 2:1. It is contemplated that any and all values or ranges of values between those described may also be utilized. The stoichiometry of the reaction should be tailored to prevent from forming a gelled product that is insoluble in a carrier solvent.

For the ingredients relative to themselves (excluding solvent as an ingredient) the hydrosilylation reaction product typically comprises: 1 to 90 wt %, alternatively 20 to 75 wt %, or alternatively 30 to 50 wt % of SiH functional organopolysiloxane (c), 1 to 90 wt %, alternatively 10-75 wt %, or alternatively 35 to 60 wt % alkenyl functional silicone resin (a), and 0.2 to 35 wt %, alternatively 2.0 to 25 wt %, or alternatively 5 to 15 wt % alkenyl polyether (b). In the total formulation including the solvent the amounts are 0.2 to 54 wt %, or alternatively 5 to 42 wt %, or alternatively 9 to 25 wt % SiH functional organopolysiloxane (c), 0.2 to 54 wt %, or alternatively 2.5 to 42 wt %, or alternatively 10.5 to 30 wt % alkenyl functional silicone resin (a), 0.04 to 21 wt %, alternatively 0.5-14 wt %, or alternatively 1.5 to 7.5 wt % alkenyl polyether (b), and 40 to 80 wt %, alternatively 45-75 wt %, or alternatively 50 to 70 wt % carrier solvent (e). In all embodiments, the hydrosilylation product should remain in solution and should not gel.

The components containing groups capable of reacting with SiH functionalities (e.g. alkenyl functional silicone resin (a) and the alkenyl polyether(b)) can be varied relative to one another to produce the desired ratio of total alkenyl groups to SiH functionality. For example the contribution of total moles of alkenyl groups could be normalized and divided between the alkenyl functional silicone resin and the alkenyl polyether. For example, the normalized moles of alkenyl groups on the alkenyl polyether could range relative to the normalized moles of alkenyl groups on the alkenyl functional silicone resin typically from 10:1 or 1:10.

An advantageous embodiment of the present invention is the post addition of a non-functional silicone resin (Component (II)) to the hydrosilylation product to improve rub-off resistance of a film of the product. In the preferred embodiment, the non-functional silicone resin (II) is added to the hydrosilylation reaction product in the carrier solvent to increase the overall MQ content of the solution. In applications where the combination of silicone resin (II) and a polyorganosiloxane is delivered in the presence of a carrier solvent, advantageous benefits are realized after the volatile carrier has evaporated from the product resulting in a film. The film is then represented solely as a combination of silicone resin (II) and a polyorganosiloxane. In these instances, the film can be described as having a silicone resin content relative to the total of all non-volatile components. In this invention, the alkenyl functional silicone resin (a) and the non-functional silicone resin (II) are considered to both contribute to the silicone resin content in the non-volatile components in which the non-volatile components can refer to the hydrosilylation product of the desired reaction.

In one embodiment, the non-functional silicone resin (II) is added to the hydrosilylation product (I) to achieve a total resin content relative to the total of all non-volatile components of 45 to 90 wt % silicone resin (II), alternatively 55 to 80 wt % silicone resin (II); and alternatively 65 to 75 wt % silicone resin (II).

In a further embodiment, the non-functional silicone resin (II) is added prior to the hydrosilylation reaction which produces component (I). The non-functional silicone resin (II) could be added to the hydrosilylation reaction product (I) as a solution in the same solvent as that utilized for the hydrosilylation reaction product (I) or in a different solvent. Alternatively, the non-functional silicone resin (II) could be added to the hydrosilylation reaction product (I) as a solid free from a solvent either as a powder or as a flake.

The combination of the hydrosilylation reaction product (I) and non-functional silicone resin (II) can be delivered in the carrier solvents used for the hydrosilylation reaction. Alternatively, the combination of the hydrosilylation reaction product (I) and non-functional silicone resin (II) can be solvent exchanged such that the initial solvent is removed and the combination is delivered in a secondary carrier solvent or blend of solvents. In another embodiment, the combination of the hydrosilylation reaction product (I) and non-functional silicone resin (II) can be delivered as a solid flake or powder. In a further embodiment, the combination will be passed through a twin screw extruder to remove solvent and flaked.

Component (B) is at least one cosmetic ingredient. The cosmetic ingredient may comprise at least one ingredient selected from a pigment; a UV stabilizer; a thermal stabilizer; a rheology modifier; a thickener; an adhesion promoter; a biocide; a preservative; an enzyme; a peptide; a pressure sensitive adhesive, or any surface active agent, a UV screen agent, or an active pharmaceutical ingredient (API).

Therapeutic active agents which may be employed as Component (B) include, for example, anti-acne agents, antibiotic, antiseptic, antifungal, antibacterial, antimicrobial, biocides, anti-inflammatory, astringents, hormones, anticancer agents, smoking cessation compositions, cardiovascular, histamine blocker, bronchodilator, analgesic, anti-arrhythmic, antihistamine, alpha-I blocker, beta blocker, ACE inhibitor, diuretic, antiaggregant, sedative, tranquilizer, anticonvulsant, anticoagulant agents, vitamins, antiaging agents, agents for treating gastric and duodenal ulcers, anticellulites, proteolytic enzymes, healing factors, cell growth nutrients, peptides and others. Specific examples of suitable therapeutic active agents include silver derivatives, penicillins, cephalosporins, tetracyclines, macrolides, epinephrine, amphetamines, aspirin, acetominophen, barbiturates, catecholamines, benzodiazepine, thiopental, codeine, morphine, procaine, lidocaine, benzocaine, sulphonamides, ticonazole, perbuterol, furosamide, prazosin, prostaglandins, salbutamol, indomethicane, diclofenac, glafenine, dipyridamole, theophylline and retinol.

In addition to the therapeutic or diagnostic materials, active ingredients may be cosmetics such as perfumes, UV protectors, shaving products, deodorants or the like. Suitable cosmetics are known to those skilled in the art. The proportion of the active agent employed in the present invention is chosen in accordance with the concentration of the active agent required in the composition to deliver the dosage required at the proposed delivery rate. This may vary within a wide range such as from 0.1 to about 70 weight percent, preferably 0.1 to 20 weight percent, of the final composition.

Component (B) can also comprise colorants, colored indicators, other diluents, extenders such as silicone fluids, silicone resins, excipients employed in pharmacy, compounds intended to perform as pH buffers in controlling the environment immediately in and around the formulation, stabilizers, preservatives, surfactants for cellular formulations such as fluorinated silicones, processing aids such as cyclic or linear polydiorganosiloxanes, bioadhesive materials, and hydrophilic, modulating and swellable components or polymers as set forth in EP Publication 465,744. Still other additional ingredients include absorbents for wounds, alginate, polysaccharides, gelatin, collagen, and materials that can decrease the friction on the surface of the cured film and/or change its gloss.

Some additional examples of the cosmetics, personal care, and cosmeceutical ingredients and pharmaceutical excipients that may be used herein may be found in the CTFA ingredient Database and the handbook of pharmaceutical excipients and can include, for example, essential oils, absorbents, anticacking agents, antioxidants, antistatic agents, astringents, binders, buffering agents, bulking agents, chelating agents, colorants, cosmetic astringents, cosmetic, biocides, deodorant agents, emollients, external analgesics, film formers, flavoring agents, fragrance ingredients, humectants, lytic agents, moisturizing agents, occlusivity enhancers, opacifying agents, oxidizing and reducing agents, penetration enhancers, pesticides, plasticizers, preservatives, skin bleaching agents, skin conditioning agents, skin protectants, slip modifiers, solubilizing agents, solvents, sunscreen agents, surface modifiers, surfactants and emulsifying agents, suspending agents, thickening agents, viscosity controlling agents including increasing or decreasing agents, or UV light absorbers.

Cosmetic, personal care and cosmeceutical ingredients, and pharmaceutical excipients which may be used as Component (B) also include alcohols, fatty alcohols and polyols, aldehydes, alkanolamines, alkoxylated alcohols (e.g. polyethylene glycol derivatives of alcohols and fatty alcohols), alkoxylated amides, alkoxylated amines, alkoxylated carboxylic acids, amides including salts (e.g. ceramides), amines, amino acids including salts and alkyl substituted derivatives, esters, alkyl substituted and acyl derivatives, polyacrylic acids, acrylamide copolymers, adipic acid copolymers, alcohols, aminosilicones, biological polymers and derivatives, butylene copolymers, carbohydrates (e.g. polysaccharides, chitosan and derivatives), carboxylic acids, carbomers, esters, ethers and polymeric ethers (e.g. PEG derivatives, PPG derivatives), glyceryl esters and derivatives, halogen compounds, heterocyclic compounds including salts, hydrophilic colloids and derivatives including salts and gums (e.g. cellulose derivatives, gelatin, xanthan gum, natural gums), imidazolines, inorganic materials (clay, TiO2, ZnO), ketones (e.g. camphor), isethionates, lanolin and derivatives, organic salts, phenols including salts (e.g. parabens), phosphorus compounds (e.g. phosphate derivatives), polyacrylates and acrylate copolymers, protein and enzymes derivatives (e.g. collagen), synthetic polymers, salts, siloxanes and silanes, sorbitan derivatives, sterols, sulfonic acids and derivatives and waxes.

Component (B) can also comprise essential oils such as Arnica (*Arnica montana*), Basil (*Ocimum basilicum*), Bergamot (*Citrus bergamia*), Cedarwood (*Cedrus atlantica*), Chamomile Roman (*Chamaemelum nobile*), Cinnamon (*Cinnamomum cassia*), Cinnamon Bark (*Cinnamomum verum*), *Cistus labdanum* (*Cistus ladanifer*), Clary Sage (*Salvia sclarea*), Clove (*Syzygium aromaticum*) Eugenol, Coriander (*Coriandrum sativum*), Cypress (*Cupressus sempervirens*), Dill (*Anethum graveolens*), Elemi (*Canarium luzonicum*), Eucalyptus dives (*Eucalyptus dives*), Eucalyptus globulus (*Eucalyptus globulus*), Eucalyptus polybractea (*Eucalyptus polybractea*), Eucalyptus radiata (*Eucalyptus radiata*), Fennel (*Foeniculum vulgare*), Fir Douglas (*Pseudotsuga menziesii*), Fir White (*Abies grandis*), Frankincense (*Boswellia carteri*), Galbanum (*Ferula gummosa*), Geranium (*Pelargonium graveolens*), Ginger (*Zingiber officinale*), Goldenrod (*Solidago canadensis*), Gotu Kola (*Centella asiatica*), Grapefruit (*Citrus paradisi*), Helichrysum (*Helichrysum italicum*), Hyssop (*Hyssopus officinalis*), Idaho Balsam Fir (*Abies balsamea*), Idaho Balsam Fir (*Abies balsamea*), Jasmine (*Jasminum officinale*), Juniper (*Juniperus osteosperma, Juniperus scopulorum*), *Laurus nobilis* (*Laurus nobilis*), Lavender (*Lavandula angustifolia*), Ledum (*Ledum groenlandicum*), Lemon (*Citrus limon*), Lemongrass (*Cymbopogon flexuosus*), Marjoram (*Origanum majorana*), Melaleuca alternifolia Or Tea Tree Oil (*Melaleuca alternifolia*), Melaleuca ericifolia (*Melaleuca ericifolia*), Melissa (*Melissa officinalis*), Mountain Or Winter Savory (*Satureja montana*), Myrrh (*Commiphora myrrha*), Myrtle (*Myrtus communis*), Nutmeg (*Myristica fragrans*), Orange (*Citrus aurantium*), Oregano (*Origanum compactum*), Palmarosa (*Cynopogon martinii*), Patchouly (*Pogostemon cablin*), Pepper, Black (*Piper nigrum*), Peppermint (*Mentha piperita*), Petit Grain (*Citrus aurantium*), Pine (*Pinus sylvestris*), Ravensara (*Ravensara aromatica*), Rose (*Rosa damascena*), Rosemary (*Rosmarinus officinalis*), Rosewood (*Aniba rosaeodora*), Sage (*Salvia officinalis*), Sandalwood (*Santalum album*), Spearmint (*Mentha spicata*), Spikenard (*Nardostachys jatamansi*), Spruce (*Picea mariana*), St John's Wort (*Hypericum perforatum*), Tangerine (*Citrus reticulata*), Tansy Idaho (*Tanacetum vulgare*), Tarragon (*Artemisia dracunculus*), Thyme (*Thymus vulgaris*), Tsuga (*Tsuga canadensis*), Valerin (*Valariana officinalis*), Vetiver (*Vetiveria zizanioides*), Western Red Cedar (*Thuja plicata*), Wintergreen (*Gaultheria procumbens*), Ylang Ylang (*Cananga odorata*), or any combination thereof.

Component (B) can also include antiacne agents such as salicylic acid, benzoyl peroxide, vitamins, and sulfur, and non-limiting examples of antifungal agents are calcium undecylenate, undecylenic acid, zinc undecylenate, and povidone-iodine.

Component (B) can also include antimicrobial agents and biocides such as alcohols, benzalkonium chloride, benzethonium chloride, hydrogen peroxide, methylbenzethonium chloride, phenol, poloxamer 188, povidone-iodine, polyhexamethylene biguanide hydrochloride, silver derivatives including salt and nano silver, and xylitol.

Component (B) can also comprise antioxidants such as acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *Camellia sinensis* oil, chitosan ascorbate, chitosan glycolate, chitosan salicylate, chlorogenic acids, cysteine, cysteine HCl, decyl mercaptomethylimidazole, erythorbic acid, d-limonene, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, Isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (*Melaleuca alternifolia*) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, and zinc dibutyldithiocarbamate.

Component (B) can also contain cosmetic biocides such as aluminum phenolsulfonate, ammonium phenolsulfonate, bakuchiol, benzalkonium bromide, benzalkonium cetyl phosphate, benzalkonium chloride, benzalkonium saccharinate, benzethonium chloride, potassium phenoxide, benzoxiquine, benzoxonium chloride, bispyrithione, boric acid, bromochlorophene, camphor benzalkonium methosulfate, captan, cetalkonium chloride, cetearalkonium bromide, cetethyldimonium bromide, cetrimonium bromide, cetrimonium chloride, cetrimonium methosulfate, cetrimonium saccharinate, cetrimonium tosylate, cetylpyridinium chloride, chloramine T, chlorhexidine, chlorhexidine diacetate, chlorhexidine digluconate, chlorhexidine dihydrochloride, p-chloro-m-cresol, chlorophene, p-chlorophenol, chlorothymol, chloroxylenol, chlorphenesin, ciclopirox olamine, climbazole, cloflucarban, clotrimazole, coal tar, colloidal sulfur, o-cymen-5-ol, dequalinium acetate, dequalinium chloride, dibromopropamidine diisethionate, dichlorobenzyl alcohol, dichlorophene, dichlorophenyl imidazoldioxolan, dichloro-m-xylenol, diiodomethyltolylsulfone, dimethylol ethylene thiourea, diphenylmethyl piperazinylbenzimidazole, domiphen bromide, 7-ethylbicyclooxazolidine, fluorosalan, formaldehyde, glutaral, hexachlorophene, hexamidine, hexamidine diisethionate, hexamidine diparaben, hexamidine paraben, hexetidine, hydrogen peroxide, hydroxymethyl dioxoazabicyclooctane, ichthammol, isopropyl cresol, lapyrium chloride, lauralkonium bromide, lauralkonium chloride, laurtrimonium bromide, laurtrimonium chloride, laurtrimonium trichlorophenoxide, lauryl isoquinolinium bromide, lauryl isoquinolinium saccharinate, laurylpyridinium chloride, mercuric oxide, methenamine, methenammonium chloride, methylbenzethonium chloride, myristalkonium chloride, myristalkonium saccharinate, myrtrimonium bromide, nonoxynol-9 iodine, nonoxynol-12 iodine, olealkonium chloride, oxyquinoline, oxyquinoline benzoate, oxyquinoline sulfate, PEG-2 coco-benzonium chloride, PEG-10 coco-benzonium chloride, PEG-6 undecylenate, PEG-8 undecylenate, phenol, o-phenylphenol, phenyl salicylate, piroctone olamine, sulfosuccinylundecylenate, potassium o-phenylphenate, potassium salicylate, potassium troclosene, propionic acid, PVP-iodine, quaternium-8, quaternium-14, quaternium-24, sodium phenolsulfonate, sodium phenoxide, sodium o-phenylphenate, sodium shale oil sulfonate, sodium usnate, thiabendazole, 2,2'-thiobis(4-chlorophenol), thiram, triacetin, triclocarban, triclosan, trioctyldodecyl borate, undecylenamidopropylamine oxide, undecyleneth-6, undecylenic acid, zinc acetate, zinc aspartate, zinc borate, zinc chloride, zinc citrate, zinc cysteinate, zinc dibutyldithiocarbamate, zinc gluconate, zinc glutamate, zinc lactate, zinc phenolsulfonate, zinc pyrithione, zinc sulfate, and zinc undecylenate.

Component (B) can also contain external analgesics such as benzyl alcohol, capsicum oleoresin (*Capsicum frutescens* oleoresin), methyl salicylate, camphor, phenol, capsaicin, juniper tar (*Juniperus oxycedrus* tar), phenolate sodium (sodium phenoxide), capsicum (*Capsicum frutescens*), menthol, resorcinol, methyl nicotinate, and turpentine oil (turpentine). Oxidizing agents suitably employable include, for example, ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, and zinc peroxide, while reducing agents suitably employable include, for example, ammonium bisufite, ammonium sulfite, ammonium thioglycolate, ammonium thiolactate, cystemaine hcl, cystein, cysteine HCl, ethanolamine thioglycolate, glutathione, glyceryl thioglycolate, glyceryl thioprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, and zinc formaldehyde sulfoxylate.

Component (B) can also contain skin bleaching active agents such as hydroquinone, and skin protectants such as allantoin, aluminum acetate, aluminum hydroxide, aluminum sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, and zinc oxide.

Component (B) can also comprise sunscreen agents such as aminobenzoic acid, cinoxate, diethanolamine methoxycinnamate, digalloyl trioleate, dioxybenzone, ethyl 4-[bis(hydroxypropyl)]aminobenzoate, glyceryl aminobenzoate, homosalate, lawsone with dihydroxyacetone, menthyl anthranilate, octocrylene, octyl methoxycinnamate, octyl salicylate, oxybenzone, padimate O, phenylbenzimidazole sulfonic acid, red petrolatum, sulisobenzone, titanium dioxide, and trolamine salicylate, and examples specifically of UV light absorbing agents include acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic acid, benzyl salicylate, bornelone, bumetriozole, butyl methoxydibenzoylmethane, butyl PABA, ceria/silica, ceria/silica talc, cinoxate, dea-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium d istyrylbiphenyl triaminotriazine stilbened isulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, octyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, tea-phenylbenzimidazole sulfonate, tea-salicylate, terepbthalylidene dicamphor sulfonic acid, titanium dioxide, triPABA panthenol, urocanic acid, or va/crotonates/methacryloxybenzophenone-1 copolymer.

The cosmetic compositions can be stored in a plurality of containers prior to use to inhibit curing or inhibition when co-formulated with excipients and actives prior to use.

Suitable containers include, for example, single use containers (e.g., foil packets, tubes, soft capsules, blisters, wipes) or multiple use containers (e.g. roll-on, tube with foam pad, pen like system, pumps and sprays, brush-in-bottle). It is often desirable to put a diluent in both containers.

The cosmetic composition is applied to the desired site or, alternatively, the component materials of the invention can be applied onto the desired site in a manner that causes mixing. Preferably, the cosmetic compositions are applied on a biological surface including, but not limited to animal bodies (e.g., human or other animal) and flora.

The cosmetic compositions of the invention can be applied, for example, by rubbing, painting, spraying, wiping, or any other conventional method of applying thin films.

The resultant films formed after application of the cosmetic composition are typically thin and non-tacky. Films on the order of up to 500 microns (e.g., 2.5 microns to 250 microns) are often obtained. These films can have many physical properties from gels to elastomers so that they are able to withstand many of the pressures exerted during normal activities.

The invention allows for a film former that can be applied to skin in order to form a protective barrier and deliver a cosmetic active. The success criteria are film forming property, non-stinging, substantivity (e.g. long lasting wear time), resistance to water, removability, adjustable permeability, permeability to actives, ability to be co-formulated, and stability. The cosmetic composition may be in the form of a cream, a gel, a powder, a paste, or a freely pourable liquid. Generally, such compositions can be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

Examples of products which can contain the cosmetic compositions of this invention include skin care creams, skin care lotions, moisturizers, facial treatments, such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including anti-acne, dental hygienic, antibiotic, healing promotive, nutritive and the like, which may be preventative and/or therapeutic. In general, the personal care composition may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. Suitable carriers are appreciated in the art.

EXAMPLES

Formulation Materials:
Synthetic Ingredients:
SiH Polymer 1—an SiH organopolysiloxane polymer having the formula $H(CH_3)_2SiO((CH_3)_2SiO)_{100}Si(CH_3)_2H$, Calculated Mw=7668; Calculated wt % SiH=0.0261 wt %
Vinyl MQ Resin 1—an alkenyl functional MQ resin having the formula $((CH_3)_3SiO_{1/2})_{0.45}(CH_2=CH(CH_3)_2SiO_{1/2})_{0.04}(SiO_{4/2})_{0.51}$ containing: 1.2 wt % vinyl, 1.0 wt % OH—solvent exchanged into isododecane and delivered as a 60% solution, Mn=7010; Mw=20700
Solid MQ Resin 1—an MQ resin having the formula $((CH_3)_3SiO_{1/2})_{0.44}(SiO_{4/2})_{0.56}$ dissolved into isododecane at 70% solids
Solid MQ Resin 2—an MQ resin having the formula $((CH_3)_3SiO_{1/2})_{0.44}(SiO_{4/2})_{0.56}$ dissolved into ethyl acetate at 70% solids. Mn=3600; Mw=23000
Polyether 1—a bis-methallyl terminated poly(ethylene oxide) having the formula $CH_2=C(CH_3)CH_2-O-(CH_2CH_2O)_{14}-CH_2(CH_3)C=CH_2$
Polyether 2—a bis-methallyl terminated poly(propylene oxide) having the formula $CH_2=C(CH_3)CH_2-O-(CH_2CH_2CH_2O)_7-CH_2(CH_3)C=CH_2$
Platinum Catalyst—a 1.0 wt % solution in isopropanol of Pt (IV) complexes with 1,3-diethenyl-1,1,3,3-tetramethyldisiloxane
Isododecane—2,2,4,6,6-pentamethylheptane
Ethyl acetate
Isobutyl acetate
Propyl propionate
2-propanol
Cosmetic Ingredients:
Emulsifier Blend: Lauryl, PEG-10, and a tris(trimethylsilyl) modified polydimethylsiloxane (also known as an alkyl, polyethoxylated, silyl dendrimer—modified polydimethylsiloxane) having the following formula:

Sodium Chloride

Glycerin

Phenoxyethanol—Euxyl® PE 9010—Schulke & Mayr GmbH

Iron Oxide (C177499), Dimethicone—SA-C335000-10/ Miyoshi Europe S.A.S.

Iron Oxide (C177491), Dimethicone—SA-C332199-10/ Miyoshi Europe S.A.S.

Iron Oxide (C177492), Dimethicone—SA-C331700-10/ Miyoshi Europe S.A.S.

Titanium Dioxide, Dimethicone—SA-TAO-77891/ Miyoshi Europe S.A.S.

Caprylyl Methicone (also known as 3-octyl, heptamethyltrisiloxane) having the formula:

Benchmark Materials (Control):

Fluid 1—a 50% solution of an MQ resin having the formula $((CH_3)_3SiO_{1/2})_{0.44}(SiO_{4/2})_{0.56}$ in decamethylcyclopentasiloxane Fluid 2—a 75% solution of silicone resin having the formula $((CH_3CH_2CH_2)SiO_{3/2})_{1.0}$ in isododecane Acrylate Copolymer—a 40% solution of methacrylate/ butyl acrylate co-polymer with a siloxane dendrimer in isododecane Example Method A A 500 mL three-neck, round bottom flask equipped with a condenser and a nitrogen line, a glass stir shaft, a PTFE stir paddle, and a thermocouple were utilized in this reaction. For Example A1: to the flask, 38.35 grams of SiH Polymer 1, 53.24 grams Vinyl MQ Resin 1, 9.77 grams Polyether 1, and 58.76 grams of 2-propanol (solvent) were added. The contents of the flask were stirred at 250 rpm and heated to 70° C. Once the temperature reached or exceeded 70° C., the Platinum Catalyst Solution (containing 20 ppm Platinum relative to the entire formulation) was added. The mixture was allowed to react for 2 hours. At the conclusion of this time, heating was discontinued and the product collected. This same procedure was used to make Examples A2 through A11 with the amounts of the ingredients shown in Table 1 below.

TABLE 1

|  | A1 | A2 | A3 | A4 | A5 | A6 |
|---|---|---|---|---|---|---|
| SiH Polymer 1 (grams) | 38.35 | 38.35 | 38.35 | 38.35 | 38.35 | 38.35 |
| Vinyl MQ Resin 1 (grams) | 53.24 | 76.05 | 114.08 | 15.21 | 38.03 | 76.05 |
| Polyether 1 (grams) | 9.77 | 7.51 | 3.76 | — | — | — |
| Polyether 2 (grams) | — | — | — | 9.71 | 8.09 | 5.39 |
| Platinum Catalyst (ppm) | 20 | 20 | 20 | 20 | 20 | 20 |
| Solvent | 2-propanol | 2-propanol | 2-propanol | isododecane | isododecane | isododecane |
| Solvent Weight (grams) | 58.76 | 61.07 | 64.92 | 51.10 | 54.05 | 58.95 |
| Total (grams) | 160.12 | 182.98 | 221.11 | 114.37 | 138.52 | 178.74 |
| wt % solids | 50.0% | 50.0% | 50.0% | 50.0% | 50.0% | 50.0% |
| Vi:SiH molar ratio | 4 | 4 | 4 | 4 | 4 | 4 |
| Vi Resin/allyl Polyether Molar Ratio | 0.35 | 0.50 | 0.75 | 0.10 | 0.25 | 0.50 |
| wt % EO (solids basis) | 12.2% | 8.2% | 3.4% | — | — | — |
| wt % PO (solids basis) | — | — | — | 17.0% | 11.7% | 6.0% |

|  | A7 | A8 | A9 | A10 | A11 |
|---|---|---|---|---|---|
| SiH Polymer 1 (grams) | 38.35 | 38.35 | 38.35 | 38.35 | 38.35 |
| Vinyl MQ Resin 1 (grams) | 114.08 | 76.05 | 76.05 | 76.05 | 38.03 |
| Polyether 1 (grams) | — | 1.35 | 2.7 | 4.05 | 4.05 |
| Polyether 2 (grams) | 2.7 | 5.63 | 3.76 | 1.88 | 5.63 |
| Platinum Catalyst (ppm) | 20 | 20 | 20 | 20 | 20 |
| Solvent | isododecane | isododecane | isododecane | isododecane | isododecane |
| Solvent Weight (grams) | 63.86 | 60.54 | 60.01 | 59.48 | 55.64 |
| Total (grams) | 218.99 | 181.92 | 180.87 | 179.81 | 141.7 |
| wt % solids | 50.0% | 50.0% | 50.0% | 50.0% | 50.0% |
| Vi:SiH molar ratio | 4 | 4 | 4 | 4 | 4 |
| Vi MQ Resin/Polyether Molar Ratio | 0.75 | 0.50 | 0.50 | 0.50 | 0.25 |
| wt % EO (solids basis) | — | 6.2% | 4.2% | 2.1% | 8.0% |
| wt % PO (solids basis) | 2.5% | 1.5% | 3.0% | 4.5% | 5.7% |

Example Method B

A 1000 mL three-neck, round bottom flask equipped with a condenser and a nitrogen line, a glass stir shaft, a PTFE stir paddle, and a thermocouple were utilized in this reaction. To the flask, 280 grams of Solid MQ Resin 1 and 120 grams of isododecane were added. The contents of flask were heated to 35° C. and stirred until the solution was transparent and no remaining solid resin was observed. This method was used to produce MQ Resin Solution 1 (% solids=68.90%). This method was used to also produce MQ Resin Solution 2 (% solids=70.85%)

Example Method C

MQ Resin Solution 1 was then combined with the reaction products from Formulations A1-A11 prepared according to Experimental Method A. The combined solutions were mixed on a Dental Mixer to produce a homogeneous solution. The resulting film forming compositions were labeled C1-C11 and are shown in Table 2 below.

TABLE 2

|  | C1 | C2 | C3 | C4 | C5 | C6 |
|---|---|---|---|---|---|---|
| Experimental A Formulation | A1 | A2 | A3 | A4 | A5 | A6 |
| Experimental A Formulation wt (grams) | 19.32 | 21.16 | 20.73 | 22.22 | 21.65 | 21.27 |
| MQ Resin Solution 1 wt (grams) | 17.57 | 9.26 | 3.69 | 24.77 | 16.91 | 8.74 |
| Resin content (solids basis) | 73% | 70% | 70% | 66% | 67% | 68% |

|  | C7 | C8 | C9 | C10 | C11 |
|---|---|---|---|---|---|
| Experimental A Formulation | A7 | A8 | A9 | A10 | A11 |
| Experimental A Formulation wt (grams) | 20.65 | 21.59 | 21.52 | 21.28 | 21.9 |
| MQ Resin Solution 1 wt (grams) | 3.61 | 9.08 | 8.99 | 8.78 | 17.28 |
| Resin content (solids basis) | 71% | 71% | 70% | 69% | 69% |

Foundation Formulation

The process to create the foundation was to mix phase A in a speed mixer at 2750 rpm for 1 minute. The amount of isododecane in the formulation was adjusted relative to the amount of solvent contained in the Film-Former (C1-C11) to bring the total of Phase A to 23 wt %. The water phase (phase B) was added in 4 equal parts with two minutes of mixing between each addition. A single phase should have resulted between each addition but if it did not, the solution was mixed longer before any further water was added. Phases A, B, and C are shown in Table 3 below. The end product formulation resulting from the mixing of Phases A, B, and C above with each of Formulations C1 through C11 above resulted in Formulations D1 through D11 which were then used as shown in Table 5 below.

TABLE 3

General Cosmetic Formulation

| | Ingredient Source | Weight (grams) |
|---|---|---|
| Phase A | | |
| Emulsifier Blend | — | 6 |
| Isododecane | — | Sum to 23 wt. % for phase A |
| Film-Former (C1 through C11) | — | 5% active |
| Phase B (Water Blend) | | |
| Water | Deionized lab water | 59.5 |
| Sodium Chloride | Fisher | 1 |
| Glycerin | Fisher | 5 |
| Phenoxyethanol, Ethylhexyglycerin | Euxyl ® PE 9010/Schülke & Mayr GmbH | 1 |
| Phase C (Pigment Blend) | | |
| Iron Oxide (CI77499), Dimethicone | SA-C335000-10/Miyoshi Europe S.A.S. | 0.07 |
| Iron Oxide (CI77491), Dimethicone | SA-C332199-10/Miyoshi Europe S.A.S. | 0.25 |
| Iron Oxide (CI77492), Dimethicone | SA-C331700-10/Miyoshi Europe S.A.S. | 1.09 |
| Titanium Dioxide, Dimethicone | SA-TAO 77891/Miyoshi Europe S.A.S. | 5.81 |
| Caprylyl Methicone | — | 3.28 |
| Total | | 100 |

TABLE 4

Masterbatches of Phase B and C in Preparation of Foundations

| Phase B (Water Blend) | Ingredient Source | wt. % | Weight (grams) |
|---|---|---|---|
| Water | | 59.5 | 1190 |
| Sodium Chloride | | 1 | 20 |
| Glycerin | | 5 | 100 |
| Phenoxyethanol, Ethylhexylglycerin | Euxyl ® PE 9010/Schülke & Mayr GmbH | 1 | 20 |

| Phase C (Pigment Blend) | Ingredient Source | wt. % | Weight (grams) |
|---|---|---|---|
| Iron Oxide (CI77499), Dimethicone | SA-C335000-10/Miyoshi Europe S. A. S. | 0.07 | 1.75 |
| Iron Oxide (CI77491), Dimethicone | SA-C332199-10/Miyoshi Europe S. A. S. | 0.25 | 6.25 |
| Iron Oxide (CI77492), Dimethicone | SA-C331700-10/Miyoshi Europe S. A. S. | 1.09 | 27.25 |
| Titanium Dioxide, Dimethicone | SA-TAO-77891/Miyoshi Europe S. A. S. | 5.81 | 145.25 |
| Caprylyl Methicone | — | 3.28 | 82 |

TABLE 5

Formulations for D1-D11, Fluid 1, Fluid 2, and Acrylate Copolymer

| Formulation Film-Former Ingredient | Control Wt. % | Fluid 1 | Fluid 2 | Acrylate Copolymer | D1 C1 | D2 C2 | D3 C3 |
|---|---|---|---|---|---|---|---|
| % Solids of Film-Former | | 50.0% | 75.0% | 40.0% | 59.3% | 55.0% | 52.3% |
| Phase A | | | | | | | |
| Emulsifier Blend (grams) | 6 | 2.40 | 2.40 | 2.40 | 2.40 | 2.40 | 2.40 |
| Isododecane (grams) | make-up | 2.80 | 4.13 | 1.80 | 3.43 | 3.16 | 2.98 |
| Film-Former (% active) | 5 | 4.00 | 2.67 | 5.00 | 3.37 | 3.64 | 3.82 |

TABLE 5-continued

Formulations for D1-D11, Fluid 1, Fluid 2, and Acrylate Copolymer

Phase B

| | | | | | | | |
|---|---|---|---|---|---|---|---|
| Water Blend (grams) | 66.5 | 26.60 | 26.60 | 26.60 | 26.60 | 26.60 | 26.60 |

Phase C

| | | | | | | | |
|---|---|---|---|---|---|---|---|
| Pigment Blend (grams) (Iron Oxides/TiO2) | 10.5 | 4.20 | 4.20 | 4.20 | 4.20 | 4.20 | 4.20 |
| Total | | 40.00 | 40.00 | 40.00 | 40.00 | 40.00 | 40.00 |

| Formulation Ingredient | D4 C4 | D5 C5 | D6 C6 | D7 C7 | D8 C8 | D9 C9 | D10 C10 | D11 C11 |
|---|---|---|---|---|---|---|---|---|
| % Solids of Film-Former | 60.9% | 58.9% | 55.7% | 52.3% | 53.4% | 54.3% | 55.0% | 57.1% |

Phase A

| | | | | | | | | |
|---|---|---|---|---|---|---|---|---|
| Emulsifier Blend (grams) | 2.40 | 2.40 | 2.40 | 2.40 | 2.40 | 2.40 | 2.40 | 2.40 |
| Isododecane (grams) | 3.51 | 3.40 | 3.21 | 2.97 | 3.06 | 3.12 | 3.16 | 3.29 |
| Film-Former (% active) | 3.29 | 3.40 | 3.59 | 3.83 | 3.74 | 3.68 | 3.64 | 3.51 |

Phase B

| | | | | | | | | |
|---|---|---|---|---|---|---|---|---|
| Water Blend (grams) | 26.60 | 26.60 | 26.60 | 26.60 | 26.60 | 26.60 | 26.60 | 26.60 |

Phase C

| | | | | | | | | |
|---|---|---|---|---|---|---|---|---|
| Pigment Blend (grams) (Iron Oxides/TiO2) | 4.20 | 4.20 | 4.20 | 4.20 | 4.20 | 4.20 | 4.20 | 4.20 |
| Total | 40.00 | 40.00 | 40.00 | 40.00 | 40.00 | 40.00 | 40.00 | 40.00 |

Testing:

Abrasion Testing

Abrasion resistance was measured on a water-in-oil foundation that contained the film formers.

The foundation was coated out using a 2 micron film gauge onto hydrated collagen (~150 micron thickness) which had been pulled over and taped to a polycarbonate block. The foundation was allowed to dry overnight in a fume hood. Using a Gardner abrasion tester fitted with an adhesive strip of the loop side of Velcro, each sample was insulted for either 50 or 20 cycles, depending on whether the film was dry or wetted with sebum. Three blocks were tested per film-forming material. Each test material was tested dry. In subsequent testing several film-formers were tested for sebum resistance which requires adding a drop of artificial sebum to the coated block and evenly spreading it out and then waiting one minute before beginning the abrasion testing.

Figure 1:
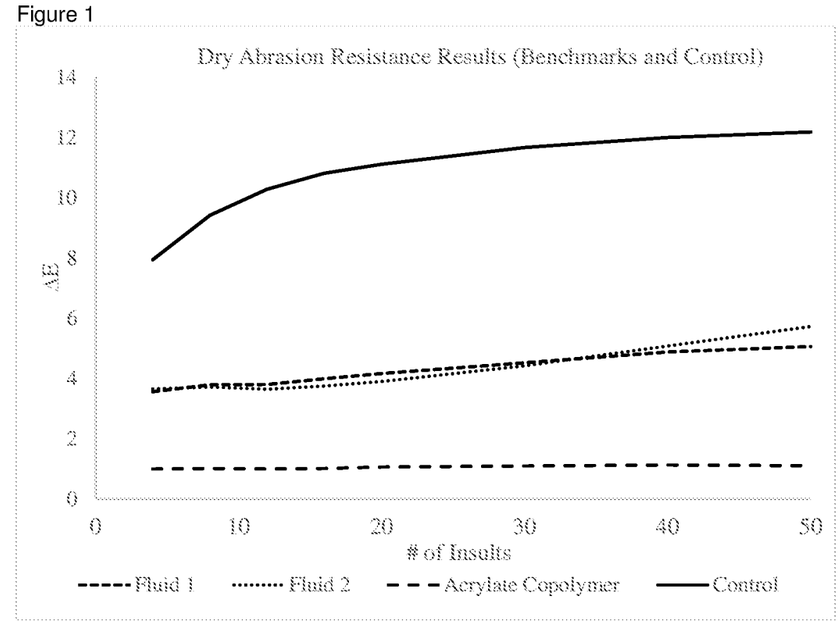
FIG. 1 provides Dry Abrasion Resistance Results for the Benchmarks and Control.
Figure 2:
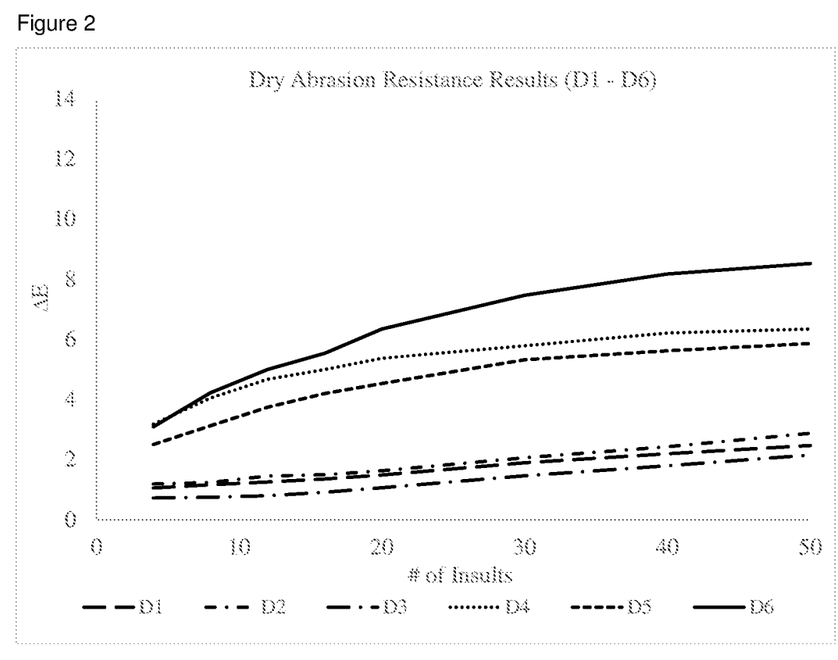
FIG. 2 provides Dry Abrasion Resistance Results for D1-D6.
Figure 3:
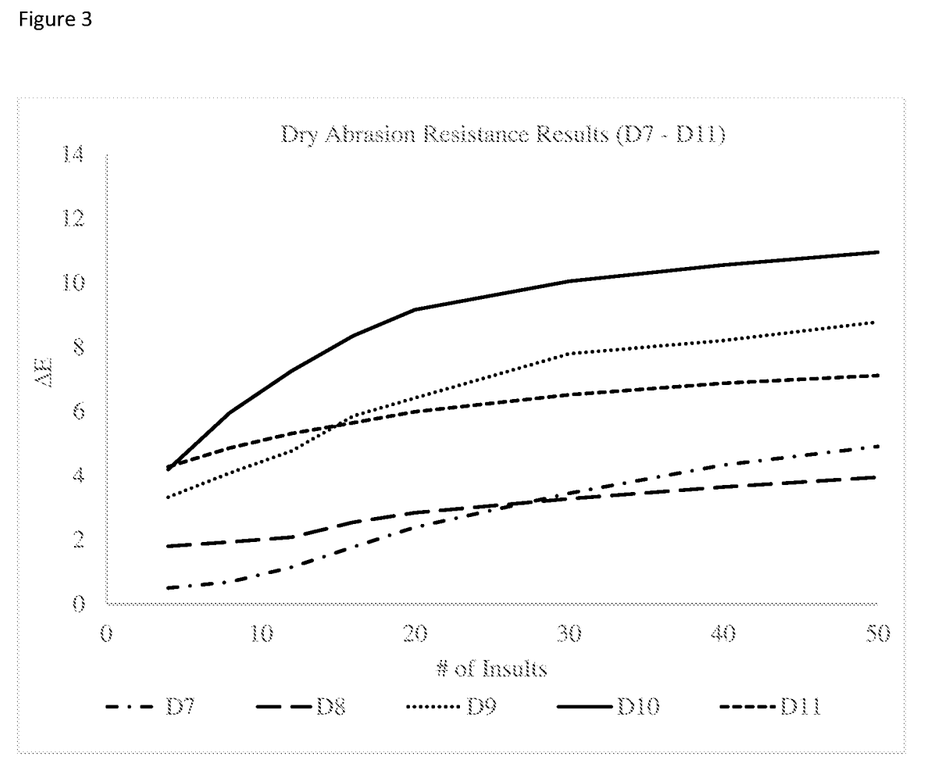
FIG. 3 provides Dry Abrasion Resistance Results for D7-D11.
Figure 4:
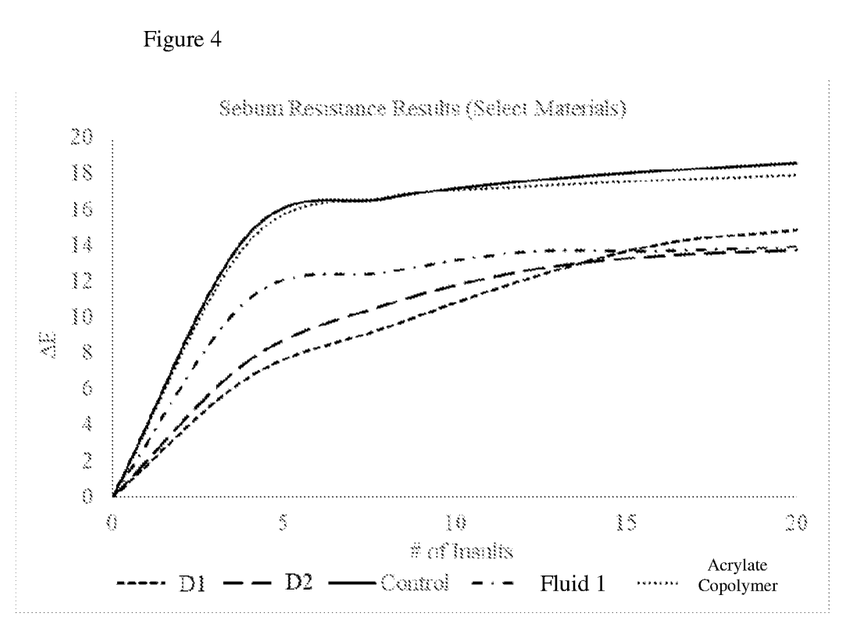
FIG. 4 provides Sebum Resistance Results for select materials.

A Hunterlab colorimeter was used to measure the LAB (color) value for each block using a 0.5" diameter filter. Measurements were taken after 0, 4, 8, 12, 16, 20, 30, 40, and 50 insults. If using sebum the testing stopped at 20 insults. From this a ΔE (or color change) was calculated to determine the resistance to abrasion. See FIGS. 1-4.

Film Flexibility and Shine

The coater and latex rubber used in this study are further mentioned below. A shine box, which is a wooden box with a light source, was utilized in order to visually measure shine. Coated rubber specimens were hung in the shine box in order to generate a clearer, more reproducible shine band for each test material.

Elastic Band—Latex Rubber:
0.33 mm thick specimens
Supplier: Four D Rubber Co. Ltd. in United Kingdom
Red latex rubber: to be used for translucent samples
White latex rubber: to be used for colored formulations
Coater:
Procedure:
1. The test material was coated onto the elastic band using a cube coater (Sheen brand ref#1103A cube).
   The substrate was affixed to a rigid and plane support (e.g. aluminum plate or table) and fastened with adhesive tape.
   The coating had a length of 10 cm and a width of ⅔ cm.
   The coating was drawn down on the shiny side of the elastic band.
   For diluted formulations, the coating thickness was 50 μm and for the fully formulated foundation the thickness was 25 μm.
2. The films were dried overnight.
3. Once the film was dry, it was affixed to the substrate on a plane support and a picture was taken before any force was applied to the coating. Film characteristics were noted before elongation: presence of cracks, shine and/or whitening effect, tackiness and film homogeneity.
4. Then a ruler was placed above the substrate to monitor the percentage of elongation. An elongation of 200% was performed.
5. After performing the elongation step, a new picture was taken. Film characteristics were noted before and after elongation; specifically, the presence of cracks, shine and/or whitening effect, tackiness and film homogeneity.

Contact Angle
Substrate:
Glass microscope slides were used as the substrate to determine water and sebum repellency of polymer coatings.
Coater:
Thin films were prepared using a cube applicator as the one supplied by Sheen Instruments. Quadruple, square or Mayer rod applicators can also be used for larger surfaces. 50 μm wet films were used when assessing film-forming properties of neat polymers (dispersed at 20 wt % in a volatile carrier) and 25 μm wet films were used when assessing the film-forming properties of finished cosmetic formulations.
Artificial Sebum Solution:
An artificial sebum with the following composition was prepared and used for sebum resistance testing:

TABLE 5

| Trade name | INCI name | Wt. % |
|---|---|---|
| glyceryl trioleate (65%, sigma) | Triolein | 60 |
| Oleic acid (grade 90% Aldrich) | Oleic acid | 20 |
| Pripure 3759 (Croda) | Squalane | 20 |

Ultrapure water (to be freshly prepared on the test day)

TABLE 6

Performance Summary for Neat and Fully-Formulated Film-Formers

| Material | Contact Angle | | Neat Film | | | Film-Forming Formulation | Foundation Abrasion (50 Insults) |
|---|---|---|---|---|---|---|---|
| | Water | Sebum | Tack | Shine | Flexibility | | |
| C1 | 107.1° | 77.6° | 3 | 4 | 4 | D1 | 4 |
| C2 | 108.4° | 78.0° | 4 | 4 | 4 | D2 | 4 |
| C3 | 104.4° | 46.7° | 4 | 4 | 4 | D3 | 4 |
| C4 | 105.5° | 28.8° | 4 | 2 | 4 | D4 | 2 |
| C5 | 108.6° | 38.0° | 4 | 3 | 4 | D5 | 3 |
| C6 | 106.0° | 46.4° | 4 | 3 | 4 | D6 | 2 |
| C7 | 104.5° | 46.0° | 4 | 2 | 4 | D7 | 3 |
| C8 | 106.5° | 66.7° | 4 | 3 | 4 | D8 | 4 |
| C9 | 105.5° | 52.1° | 3 | 1 | 4 | D9 | 2 |
| C10 | 103.3° | 49.1° | 3 | 3 | 4 | D10 | 1 |
| C11 | 107.0° | 68.9° | 3 | 3 | 4 | D11 | 2 |
| Fluid 1 | 95.9° | 33.9° | 4 | 2 | 1 | Fluid 1 | 3 |
| Fluid 2 | 97.1° | 36.0° | 2 | 3 | 3 | Fluid 2 | 3 |
| Acrylate Copolymer | 99.0° | 49.1° | 4 | 2 | 1 | Acrylate Copolymer | 4 |

Key for above table:
Tack (4 = no tack; 1 = very tacky)
Shine (4 = glossy; 1 = matte)
Flexibility after stretching (4 = highly flexible with no cracks; 1 = inflexible, cracked upon stretching)
Abrasion (4 = minimal reduction in color; 1 = substantial reduction of color)

The invention claimed is:

1. A cosmetic composition comprising:
   (A) a film forming composition that can produce a tack free surface comprising:
   (I) a hydrosilylation reaction product of:
   (a) a silicone resin having the formula:
   $(R^1R^2_2SiO_{2/2})_w(R^1R^2SiO_{2/2})_x(R^2SiO_{3/2})_y(SiO_{4/2})_z$
   wherein $R^2$ is a $C_1$ to $C_{10}$ hydrocarbon group free of aliphatic unsaturation, $R^1$ is $R^2$ or an alkenyl group, w is from 0.3 to 0.6, x is from 0.0 to 0.2, y is 0, z is from 0.4 to 0.7, w+x+y+z=1.0, and w+z is from 0.85 to 1.0, with the proviso that the silicone resin (a) has at least two silicon-bonded alkenyl groups per number average molecule;
   (b) a polyether compound having the formula: $R^3O(C_2H_4O)_c(C_3H_6O)_dR^3$ wherein $R^3$ is a monovalent unsaturated aliphatic hydrocarbon group containing 2 to 12 carbon atoms, c is from 0 to 50, d is from 0 to 50, and the value of c+d is greater than zero;
   (c) an SiH functional organopolysiloxane having the general formula: $H_cR_{3-c}SiO(R_2SiO)_a(RHSiO)_bSiR_{3-c}H_c$ wherein c is 0 or 1, R can be identical or different and is a monovalent, optionally substituted hydrocarbon group with 1 to 18 carbon atoms, a and b are integers, with the proviso that the sum of a+b is 0 to 300, and wherein the organopolysilane contains SiH in amounts from 0.01 to 0.4 wt %;
   (d) a hydrosilylation catalyst; and
   (e) carrier solvent; and
   (II) a silicone resin having the formula: $(R^4_3SiO_{1/2})_u(SiO_{4/2})_v$, wherein $R^4$ is a $C_1$ to $C_{10}$ hydrocarbon group free of aliphatic unsaturation, u is from 0.3 to 0.6, v is from 0.4 to 0.7, and the value of u+v is 1.0; and
   (B) at least one cosmetic ingredient.

2. A composition according to claim 1, wherein (a) is a silicone resin having the formula:
$(R^1R^2_2SiO_{1/2})_w(SiO_{4/2})_z$ wherein $R^1$ is vinyl, $R^2$ is methyl, w is from 0.3 to 0.6, z is from 0.4 to 0.7, and the value of w+z is 1.0.

3. A composition according to claim 2, wherein (b) is selected from
$H_2C=C(CH_3)CH_2O(C_2H_4O)_cCH_2(CH_3)C=CH_2$ or
$H_2C=C(CH_3)CH_2O(C_3H_6O)_dCH_2(CH_3)C=CH_2$
wherein c is from 0 to 14 and d is from 0 to 7.

4. A composition according to claim 3, wherein (c) is an SiH functional organopolysiloxane having the general formula: $HR_2SiO(R_2SiO)_a(RHSiO)_bSiR_2H$ wherein R is methyl and the sum of a+b is 6 to 110 and R is methyl.

5. A composition according to claim 4, wherein (d) is a platinum group metal-containing catalyst.

6. A composition according to claim 5, wherein (e) is selected from linear volatile methyl silicones selected from hexamethyldisiloxane, octamethyltrisiloxane, decamethyltetrasiloxane, dodecamethylpentasiloxane, tetradecamethylhexasiloxane, or hexadecamethylheptasiloxane, cyclic volatile methyl silicones selected from hexamethylcyclotrisiloxane, octamethylcyclotetrasiloxane, decamethylcyclopentasiloxane, or dodecamethylcyclohexasiloxane; or branch volatile methyl silicones selected from heptamethyl-3-{(trimethylsilyl)oxy}trisiloxane, hexamethyl-3,3,bis-{(trimethylsilyl)oxytrisiloxane, or pentamethyl {(trimethylsilyl)oxy}cyclotrisiloxane, non-volatile polysiloxanes selected from polydimethylsiloxane, polydiethylsiloxane, polymethylethylsiloxane, polymethylphenylsiloxane, or, polydiphenylsiloxane, or organic carrier solvents selected from isododecane, isohexadecane, ethyl acetate, ethyl alcohol, isopropyl alcohol, ester palmitate, propylene glycol, C12-15 alkyl benzoate, caprylic/capric triglyceride, coco-caprylate/caprate, diisopropyl adipate, propyl propionate, isobutyl acetate, diisostearyl fumarate, diethyl carbonate, dicaprylyl carbonate, dicaprylyl ether, propylene carbonate, diisostearyl malate, isocetyl stearate, isopropyl isostearate, isopropyl laurate, isopropyl myristate, isopropyl palmitate, isopropyl stearate, isostearyl benzoate, myristyl ether acetate w/propylene glycol, myristyl lactate, octyldodecyl stearoyl stearate, octylpalmitate, octylstearate, tridecyl neopentanoate, triisocetyl citrate, lauryl alcohol, oleyl alcohol, glyceryl trioctanate, polyglyceryl-3 diisostearate, mineral oil, dipropylene glycol, glycol ether, propylene glycol methylether acetate, propylene glycol methylether, diethylhexyl carbonate, glycerin, castor oil, lanolin oil, sunflower oil, C11-12 isoparaffin, polydecene, organic fats, oils, fatty acids, fatty alcohols, or combinations thereof.

7. A composition according to claim 6, wherein $R^4$ is methyl.

8. A composition according to claim 1, wherein $R^4$ is methyl.

9. A composition according to claim 1, wherein the cosmetic ingredient is at least one ingredient selected from a pigment, a UV stabilizer, a thermal stabilizer, a rheology modifier, a thickener, an adhesion promoter, a biocide, a preservative, an enzyme, a peptide, a pressure sensitive adhesive, a surface active agent, a UV screen agent, or an active pharmaceutical ingredient (API).

10. A composition according to claim 1, wherein:
   (a) is a silicone resin having the formula: $(R^1{}_3SiO_{1/2})_w(SiO_{4/2})_z$ wherein $R^1$ is vinyl, w is from 0.3 to 0.6, z is from 0.4 to 0.7, and the value of w+z is 1.0;
   (b) is selected from
   $H_2C=C(CH_3)CH_2O(C_2H_4O)_cCH_2(CH_3)C=CH_2$ or
   $H_2C=C(CH_3)CH_2O(C_3H_6O)_dCH_2(CH_3)C=CH_2$
   wherein c is from 0 to 14 and d is from 0 to 7;
   (c) is an SiH functional organopolysiloxane having the general formula:
   $HR_2SiO(R_2SiO)_a(RHSiO)_bSiR_2H$ wherein R is methyl and the sum of a+b is 6 to 110;
   (d) is a platinum group metal-containing catalyst;
   (e) is selected from linear volatile methyl silicones selected from hexamethyldisiloxane, octamethyltrisiloxane, decamethyltetrasiloxane, dodecamethylpentasiloxane, tetradecamethylhexasiloxane, or hexadecamethylheptasiloxane, cyclic volatile methyl silicones selected from hexamethylcyclotrisiloxane, octamethylcyclotetrasiloxane, decamethylcyclopentasiloxane, or dodecamethylcyclohexasiloxane; or branch volatile methyl silicones selected from heptamethyl-3-{(trimethylsilyl)oxy}trisiloxane, hexamethyl-3,3,bis-{(trimethylsilyl)oxy}trisiloxane, or pentamethyl {(trimethylsilyl)oxy}cyclotrisiloxane, non-volatile polysiloxanes selected from polydimethylsiloxane, polydiethylsiloxane, polymethylethylsiloxane, polymethylphenylsiloxane, or, polydiphenylsiloxane, or organic carrier solvents selected from isododecane, isohexadecane, ethyl acetate, ethyl alcohol, isopropyl alcohol, ester palmitate, propylene glycol, C12-15 alkyl benzoate, caprylic/capric triglyceride, coco-caprylate/caprate, diisopropyl adipate, propyl propionate, isobutyl acetate, diisostearyl fumarate, diethyl carbonate, dicaprylyl carbonate, dicaprylyl ether, propylene carbonate, diisostearyl malate, isocetyl stearate, isopropyl isostearate, isopropyl laurate, isopropyl myristate, isopropyl palmitate, isopropyl stearate, isostearyl benzoate, myristyl ether acetate w/propylene glycol, myristyl lactate, octyldodecyl stearoyl stearate, octylpalmitate, octylstearate, tridecyl neopentanoate, triisocetyl citrate, lauryl alcohol, oleyl alcohol, glyceryl trioctanate, polyglyceryl-3 diisostearate, mineral oil, dipropylene glycol, glycol ether, propylene glycol methylether acetate, propylene glycol methylether, diethylhexyl carbonate, glycerin, castor oil, lanolin oil, sunflower oil, C11-12 isoparaffin, polydecene, organic fats, oils, fatty acids, fatty alcohols, or combinations thereof;
   (II) is a silicone resin having the formula: $(R^4{}_3SiO_{1/2})_u(SiO_{4/2})_v$ wherein $R^4$ is methyl, u is from 0.3 to 0.6, v is from 0.4 to 0.7, and the value of u+v is 1.0; and
   (B) is selected from at least one of a filler, a pigment, a UV stabilizer, a thermal stabilizer, a rheology modifier, a thickener, an adhesion promoter, a biocide, a preservative, an enzyme, a peptide, a pressure sensitive adhesive, a surface active agent, a UV screen agent, or an active pharmaceutical ingredient (API).

11. A composition according to claim 10, wherein the hydrosilylation reaction product is produced by a method comprising mixing and optionally heating (a), (b), (c), (d), and (e).

12. A composition according to claim 11, wherein heating occurs at a temperature of 50 to 110° C.

13. A composition according to claim 10, wherein silicone resin (II) is added to the hydrosilylation product (I) to achieve a total MQ resin content relative to the total of all non-volatile components of 45 to 90 wt % silicone resin (II), alternatively 55 to 80 wt % silicone resin (II); and alternatively 65 to 75 wt % silicone resin (II).

14. A composition according to claim 1, wherein the hydrosilylation reaction product is produced by a method comprising mixing and optionally heating (a), (b), (c), (d), and (e).

15. A composition according to claim 14, wherein heating occurs at a temperature of 50 to 110° C.

16. A composition according to claim 1, wherein silicone resin (II) is added to the hydrosilylation product (I) to achieve a total MQ resin content relative to the total of all non-volatile components of 45 to 90 wt % silicone resin (II), alternatively 55 to 80 wt % silicone resin (II); and alternatively 65 to 75 wt % silicone resin (II).

17. A lip, nail, skin, or mascara product comprising the cosmetic composition of claim 1.

* * * * *